United States Patent
Castillejos

(10) Patent No.: US 7,981,096 B2
(45) Date of Patent: Jul. 19, 2011

(54) OPTIC NERVE HEAD IMPLANT AND MEDICATION DELIVERY SYSTEM

(76) Inventor: David Castillejos, La Jolla, CA (US)

( * ) Notice: Subject to any disclaimer, the term of this patent is extended or adjusted under 35 U.S.C. 154(b) by 0 days.

(21) Appl. No.: 11/801,879

(22) Filed: May 11, 2007

(65) Prior Publication Data
US 2007/0265599 A1 Nov. 15, 2007

Related U.S. Application Data

(60) Provisional application No. 60/800,253, filed on May 12, 2006.

(51) Int. Cl.
*A61F 2/14* (2006.01)
(52) U.S. Cl. ........ 604/294; 623/6.63; 128/898; 604/298
(58) Field of Classification Search .......... 604/298, 604/294; 623/6.63–6.64
See application file for complete search history.

(56) References Cited

U.S. PATENT DOCUMENTS

| | | | | |
|---|---|---|---|---|
| 4,115,544 A * | 9/1978 | Shell | | 514/10 |
| 4,853,224 A * | 8/1989 | Wong | | 424/427 |
| 4,902,292 A * | 2/1990 | Joseph | | 623/6.64 |
| 5,098,443 A * | 3/1992 | Parel et al. | | 128/898 |
| 5,207,660 A * | 5/1993 | Lincoff | | 604/300 |
| 5,378,475 A * | 1/1995 | Smith et al. | | 424/473 |
| 5,501,856 A * | 3/1996 | Ohtori et al. | | 424/428 |
| 5,527,356 A * | 6/1996 | Peyman et al. | | 623/6.63 |
| 5,554,187 A * | 9/1996 | Rizzo, III | | 623/6.16 |
| 5,634,946 A * | 6/1997 | Slepian | | 128/898 |
| 5,843,184 A * | 12/1998 | Cionni | | 623/4.1 |
| 6,196,993 B1 * | 3/2001 | Cohan et al. | | 604/891.1 |
| 6,413,540 B1 * | 7/2002 | Yaacobi | | 424/427 |
| 6,886,565 B2 * | 5/2005 | Morris et al. | | 128/846 |
| 7,090,888 B2 * | 8/2006 | Snyder et al. | | 427/2.21 |
| 7,203,351 B1 * | 4/2007 | Swindale et al. | | 382/128 |
| 2001/0004708 A1 * | 6/2001 | Nagai | | 623/4.1 |
| 2001/0008978 A1 * | 7/2001 | Zapata | | 623/6.63 |
| 2002/0182185 A1 * | 12/2002 | Wong | | 424/93.7 |
| 2003/0149479 A1 * | 8/2003 | Snyder et al. | | 623/6.16 |
| 2003/0175324 A1 * | 9/2003 | Robinson et al. | | 424/427 |
| 2004/0024453 A1 * | 2/2004 | Castillejos | | 623/4.1 |
| 2004/0133155 A1 * | 7/2004 | Varner et al. | | 604/93.01 |
| 2006/0178655 A1 * | 8/2006 | Santini et al. | | 604/891.1 |
| 2006/0258994 A1 * | 11/2006 | Avery | | 604/294 |
| 2007/0027537 A1 * | 2/2007 | Castillejos | | 623/4.1 |
| 2007/0219632 A1 * | 9/2007 | Castillejos | | 623/6.13 |
| 2007/0292475 A1 * | 12/2007 | Campbell et al. | | 424/428 |
| 2008/0167600 A1 * | 7/2008 | Peyman | | 604/20 |

* cited by examiner

*Primary Examiner* — Tatyana Zalukaeva
*Assistant Examiner* — Paula L Craig

(57) ABSTRACT

An method and a device for implant into the eye of a patient configured in size to frictionally engage within a cup-like depression naturally occurring in the optic nerve of the eye. The implant has a reservoir for calculated disbursement of medicine to tissue surrounding it and in one mode is refillable and in another mode is formed of biodegradable material which is absorbed by the patient after use ceases.

10 Claims, 4 Drawing Sheets

OPTIC NERVE HEAD IMPLANT AND MEDICATION DELIVERY SYSTEM

FIELD OF INVENTION

This application claims the benefit of U.S. Provisional Application 60/800,253 filed May 12, 2006. The device and methods herein provide for therapeutic methods and procedures for treating maladies associated with the optic nerve and/or the macula within the eye. More particularly, the device and method disclose an ocular implant adapted to anchor in the eye which is engageable to an eye mounted reservoir providing medication to the implant for delivery to various parts of the eye.

BACKGROUND

From time to time, people suffer from various maladies of the eye. Among these maladies are problems related to either the optic nerve or the macula of the eye. These problems pose a number of difficulties to a doctor as these areas are considered to be hard to reach.

In the past, therapies for the macula and/or the optic nerve have been difficult to treat. Since these areas are difficult for surgeons to reach (using standard methods and procedures), the favored treatment has been injections of medication into the vitreous cavity. This has been problematic as treatments must take place on a routine basis (typically repeated every six weeks), and such injections yield a high risk of infection inside the eye (Endophthalmitis) and discomfort to the patient from the procedures.

Consequently, there is a continuing need for a medical treatment that would require a simple surgical procedure that would have long-lasting effects to prevent or abate maladies effecting the macula and/or the optic nerve which do not require continuing injections and the resulting ongoing risk of infection and patient discomfort. Such a treatment would be further enhanced by the provision of a drug delivery system that can be modulated for dose and time that would communicate the drug directly to the vicinity of the optic nerve or macula.

In this respect, before explaining at least one embodiment of the invention in detail it is to be understood that the invention is not limited in its application to the details of construction and to the arrangement of the components set forth in the following description or illustrated in the drawings nor the steps outlined in the specification. The invention is capable of other embodiments and of being practiced and carried out in various ways as those skilled in the art will readily ascertain from reading this specification. Also, it is to be understood that the phraseology and terminology employed herein are for the purpose of description and should not be regarded as limiting.

As such, those skilled in the art will appreciate that the conception, upon which this disclosure is based, may readily be utilized as a basis for designing other methods and systems for carrying out the several purposes of the present invention of employing implants engaged to the optic nerve to provide long term drug delivery to the optic nerve and macula. It is important, therefore, that the claims be regarded as including such equivalent construction insofar as they do not depart from the spirit and scope of the present invention. Further objectives of this invention will be brought out in the following part of the specification, wherein detailed description is for the purpose of fully disclosing the invention without placing limitations thereon.

SUMMARY OF THE INVENTION

There is disclosed and described herein and method and implant component adapted for engagement in the cup portion of the optic nerve head within the patient's eye. The device and method employ an implant which features a reservoir of medication and a disbursement system adapted to disburse such medication in the area of the optic nerve and close to the macula for a duration of time. Such an implant device and the method of implantation by placement in the cup of the head of the optic nerve will serve to deliver medication directly to the eye components suffering from disease and slow or eliminate macular degeneration and/or slow or eliminate the degeneration of the optic nerve itself.

Placing the implant at the site of the problem, and employing a system to allow the medication to seep out slowly over time provides great benefit to the patient. The medication (as it seeps) will find its way to areas in the eye which are, otherwise, very difficult to reach. At the point when all of the medication has left the implant, the implant will either dissolve on its own (biodegradable), or in an alternative embodiment, can be refilled so additional medication can continue to seep over time.

The exterior dimension of the body of the apparatus for implant into an eye is dimensioned for a frictional engagement in the cup-like depression of the optic nerve of the patient. The body when implanted in the cup like depression of the optic nerve of the patient, is maintained in a mounted position by the frictional engagement, and the medicine is disbursed to the tissue of the eye. The body may be formed of biodegradable material. The biodegradable material is absorbable by the patient subsequent to disbursement of the medicine therefrom, whereby the body once implanted will dissolve over time and need not be removed surgically. The internal cavity may be refillable with the medicine by a hypodermic needle communicating through the sidewall. The internal cavity may be refilled with the medication while the implant is mounted in the eye. An aperture in the sidewall or a semipermeable membrane in the sidewall of the implant may be used for controlled disbursement of the medicine from the internal cavity.

A method of placing an ocular implant for delivery of medicine to a patient may include a step of ascertaining the dimensions of a naturally existing cup like depression in the optic nerve of a patient. Another step is determining an optimum exterior dimension for the implant in which the exterior surface of the implant will achieve a frictional engagement with the cup like depression when inserted therein in a mounted position. An implant having the optimum exterior dimension is acquired. Another step is ascertaining a medicine to be housed by the interior cavity of the implant for disbursement to the tissue of the patient, and ascertaining that the medicine is within the interior chamber. The implant is placed into the mounted position in the patient. The method may include a step of ascertaining when a refill of the medicine in the interior chamber is needed, and employing a hypodermic needle to communicate additional medicine to the interior chamber.

An object of this invention is the provision of an implant that is engageable to the optic nerve and adapted to communicate medication during such engagement.

An additional object of this invention is the provision of such an implant that alleviates the need for constant injections into the eye for treatment of optic nerve and macula maladies.

It is another object of this invention to provide such a method and apparatus which employs an implant dimensioned for placement directly into the cup location within the optic nerve head. By employing the device herein and the method and position of placement in the eye, a constant stream of medication is provided to the eye that will easily reach both the optic nerve itself and the macula (which is close by).

Another object of this invention is to provide a method employing the implant herein to deliver long term drug therapy to the optic nerve and macula section of the eye.

These together with other objects and advantages which will become subsequently apparent reside in the details of the construction and operation of the device as more fully hereinafter described and claimed, reference being had to the accompanying drawings forming a part thereof, wherein like numerals refer to like parts throughout.

BRIEF DESCRIPTION OF THE DRAWING FIGURES

DETAILED DESCRIPTION OF PREFERRED EMBODIMENTS

Figure 1:
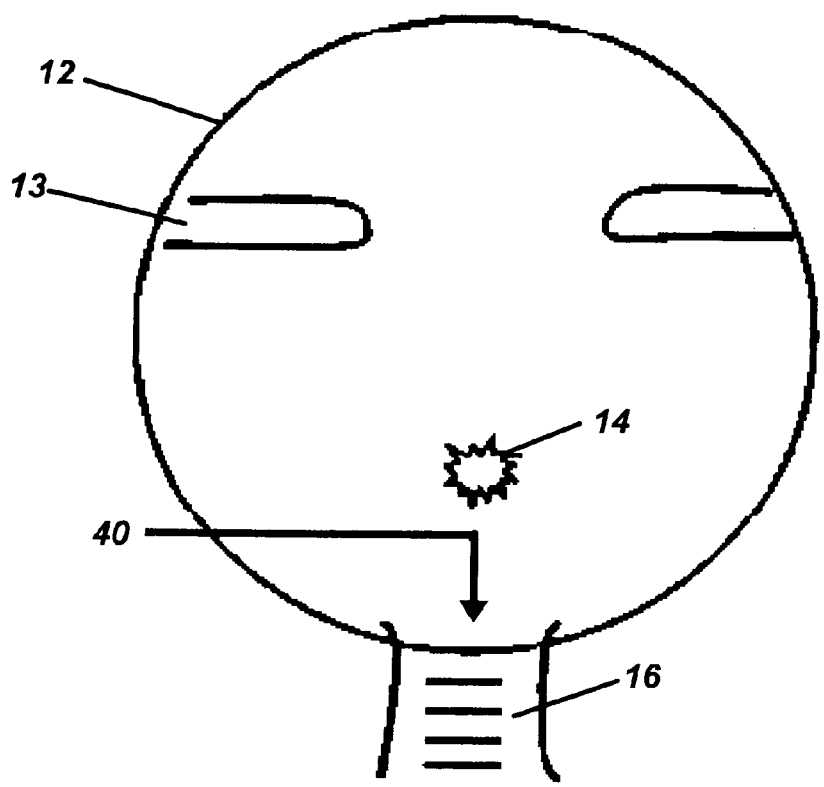
FIG. 1 depicts an overview of the eye and employment of the device and method herein in the eye.

Referring now to the drawings, FIGS. 1-7 disclose the preferred embodiments of the device and method herein which allow for the novel method of treatment using an implant 11 to treat the eye 12 and deliver medication to the macula 14 and optic nerve 16 portions of the eye 12.

As can be seen in FIG. 1, in a simple depiction to those skilled in the art there is seen the eye 12, the iris 13, the macula 14, and the optic nerve 16 located in the posterior pole of the eye 12. Also presented in FIG. 1, the optic nerve head "Cup" 40. From this figure and the other figures herein, you can see that an implant 11 can be snugly fit into this "Cup" 40 within the optic nerve 16 so medication seeping from such an implant can easily reach both the macula 14 and the optic nerve 16 itself.

In the preferred mode of the device and method the implant 11 is configured in such a way as to contain medication in an internal reservoir 20 section defined by a sidewall 22 which also defines the exterior dimension of the implant 11. Using a means for disbursement of the medication from the reservoir such as an aperture 24 or permeable membrane 26, the medication 19 which will seep out of the implant 11 slowly over time. This medication 19 housed in the reservoir 20 portion of the implant 11, as it seeps therefrom, will find its way to areas in the eye 18 which are, otherwise, very difficult to reach.

In one mode of the device and method particularly preferred, once the implant 11 is drained and all the medication has left the reservoir 20 portion of the implant 11, the implant 11 will dissolve on its own (biodegradable), and be absorbed by the body. This mode would work well with either a liquid medication such as in FIG. 5 in the reservoir 20 or a soluble solid medication therein as in FIG. 6. Or, the entire implant might be formed of the soluble medication with the sidewall 22 portion defining the dimensions of the implant 11 having a slightly slower decay rate to allow it to remain mounted in the optic nerve while the interior dissolves.

Figure 7:
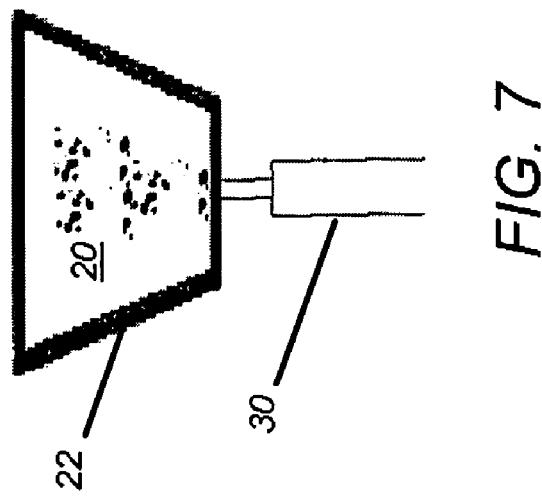
FIG. 7 depicts the implant being reloaded with medication.
Figure 5:
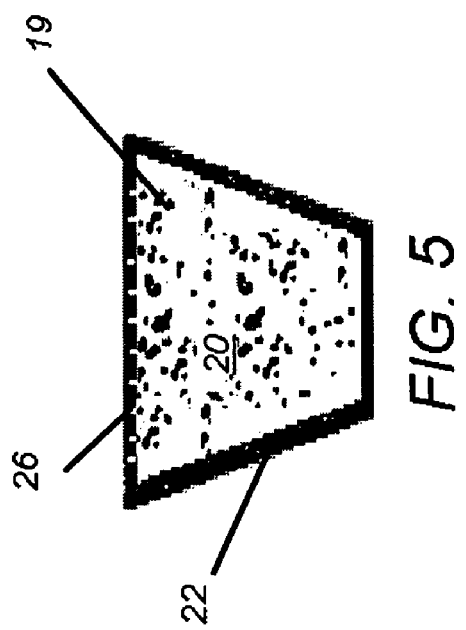
FIG. 5 depicts a sliced view of the implant with a reservoir portion containing liquid and having a permeable membrane.
Figure 6:
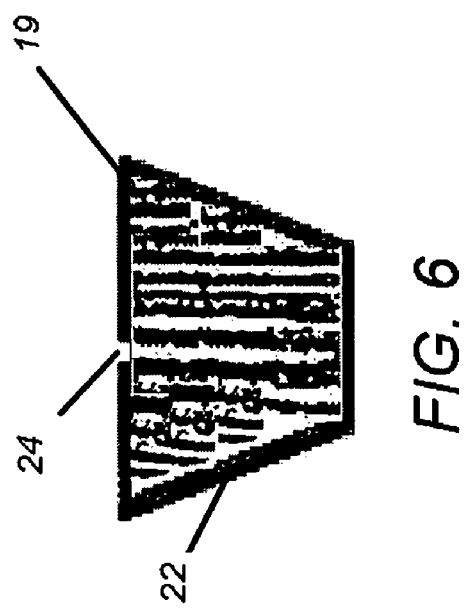
FIG. 6 depicts a sliced view of the implant having a solid or powdered medication in the reservoir and an aperture for release therefrom.

In an alterative embodiment, as shown in FIG. 7, the implant 11 can be refilled once emptied by a hypodermic needle 30. While requiring the use of shots into the eye 12 which is currently employed in prior art treatments, the patient will benefit from far fewer shots since the implant 11 can be refilled so additional medication can continue to seep over time.

Figure 2:
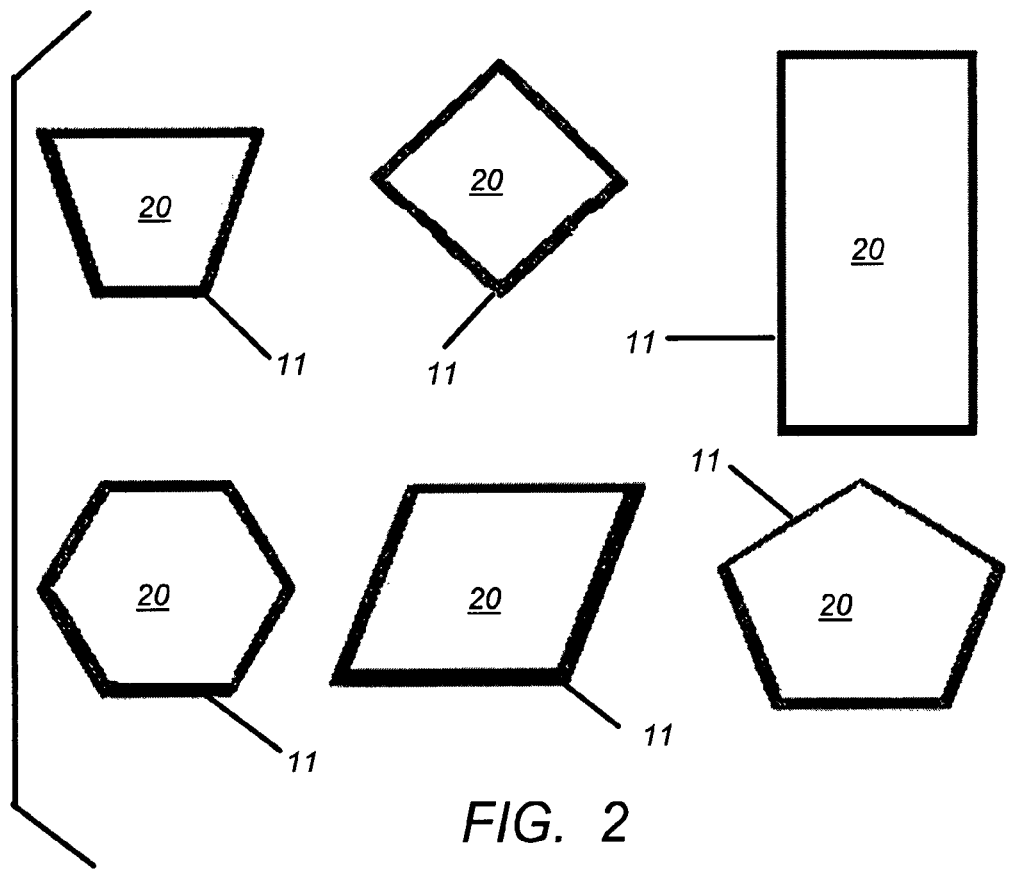
FIG. 2 depicts the various shapes that can be used for such an implant.

As shown in FIG. 2 such implants 11 can be constructed using a number of shapes and a number of different materials to form an exterior dimension suited to the implant site.

The dimensional aspects of the implant chosen should be well adapted to place the implant into the posterior pole of the eye 12. The dimension of the implant 11 employed should insure that it will be anchored in such a way as it will not move. The type of slow disbursement chosen and medication 19 employed should be adapted to continuously allow medication to seep into the eye 12.

Depending on the medical professional's treatment decisions the implant 11 can either dissolve over time or be refilled as in FIG. 7. This will allow the patient to enjoy the results of an effective treatment procedure, while minimizing risks (such as the risk of infection).

In a particularly preferred mode of the invention, the ideal location for such an implant is within the optic nerve cup 40. This cup 40 area can appropriately hold an implant for an indefinite period of time. This is due primarily to the fact that this cup area acts as a natural glove for a properly dimensioned implant 11, such that the properly dimensioned implant 11 can be wedged into the cup 40 area so it will not require any additional anchoring mechanisms.

In a preferred embodiment of the invention herein, a doctor such as an ophthalmologist will first measure the cup 40 area within the optic nerve 16 of the eye 12 for a given patient. It is typical to find that the size of this cup area is from 300 to 500 microns, however, the extremes reach from 200 to 800 microns. As soon as the doctor determines the number of microns within the eye 12 for a given patient, the doctor will decide on the best configuration and exterior dimension for the implant 11 which will be implanted into the optic nerve head cup 40 for this patient. The doctor can select from a number of configurations yielding different exterior dimensions of the implants 11 as shown in FIG. 2 which is not intended to be limiting of the shapes employed. Shown are a square, pentagon, hexagon, cylindrical shape, and rectangle, however a shape determined to fit snugly into the optic nerve head cup 40 is ultimately the appropriate dimension for the exterior of the implant 11.

Once the configuration of the implant 11 is selected by the doctor, the doctor will either create the implant using his own tools (such a lathe), or he will purchase an appropriate implant from a medical device manufacturing company that is commissioned to manufacture such implants as they are needed and adapted to the shape and dimensional characteristics determined by the doctor. Such implants 11 after they are created must be appropriately sterilized before they can be implanted in the eye.

Once the doctor has made his selection (of appropriately designed, shaped, and dimensioned sterilized implants), he or she will fill the implant with the appropriate medication 19, and a surgical procedure can be performed in order to insert the implant into the optic nerve head cup 40 so the medication can seep out over time. Once again, the optic nerve 16 itself as well as the macula 14 can benefit from this medication as it will seep in the general vicinity of the posterior pole.

As described earlier, this implant will then either dissolve itself naturally (as the last of the medication leaves the implant), or the implant can be refilled by the doctor by way of a follow-up visit by the patient to the doctor's office.

Such an implant 11 as described herein works best if adapted to provide a means for medication to seep out at a predetermined level or rate and/or quantity. There are a number of ways to achieve such predetermined seepage levels, however, the preferred embodiment for this patent application is to use a biodegradable material such as gancyclovir, however, an alternative embodiment may use a semipermeable membrane material 26 instead.

Figure 4:
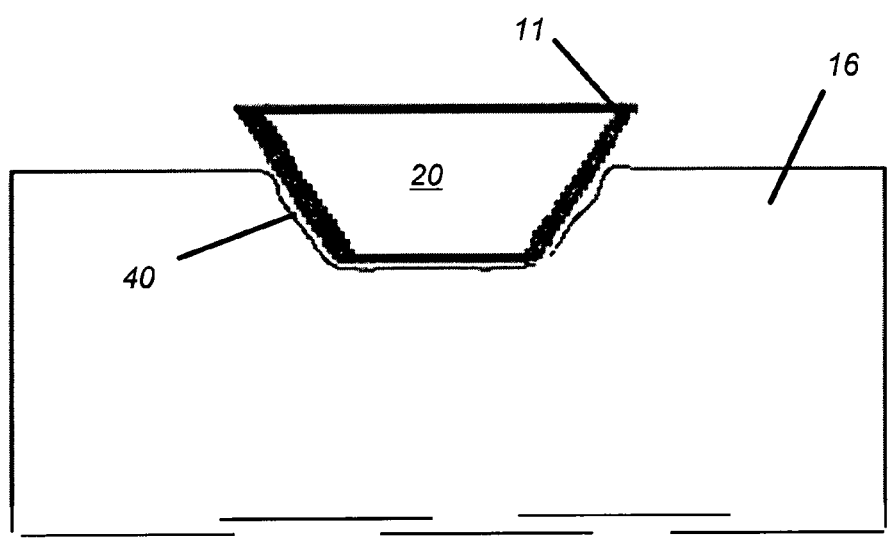
FIG. 4 shows a cross-section of the cup area within the optic nerve.
Figure 3:
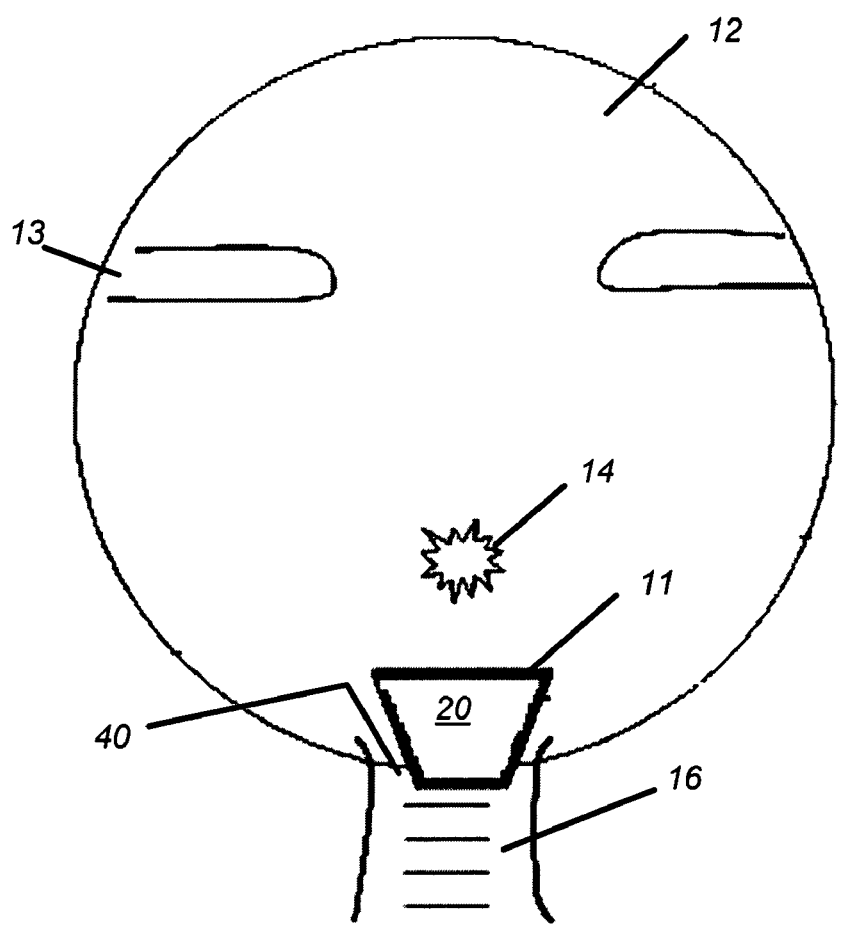
FIG. 3 shows an embodiment of the implant employed with the method herein.

As noted, and shown in FIGS. 2-4, the various shapes that can be used for such an implant 11 should be well adapted to the shape of the cup 40 in the intended patient. It is important to note that virtually any shape or three-dimensional configuration can be used as long as it fits snugly into the cup 40 of the optic nerve so it does not need any further anchoring mechanism and that it has a chosen delivery system to deliver a constant flow of medication into the posterior pole of the eye for the life of the implant. As shown in FIGS. 3 and 4, there is a frusto conical shaped implant 11 which is well adapted for a wedged engagement into the cup 40 of the optic nerve 16 head.

FIG. 4 further shows a cross-section of the Optic Nerve Head cup 40 and how it is ideal to hold such an implant 11. A particularly novel aspect of this device and method leverages the design of the optic nerve head and the manner in which the axons are placed on both side of the optic nerve head cup 40 portion. Using the disclosed design and method of placement in the cup 40 of the optic nerve 16, allows an implant 11 to be placed in the posterior pole in order to solve a number of potential maladies for patients experiencing problems with their vision. Thus, in the most preferred mode of the device allowing the method herein, the exterior dimension of the implant 11 is such that it is adapted for a wedged engagement with the optic nerve cup 40 so it can deliver medication or provide other therapies to the posterior pole region of the eye.

The device and method providing for an optic nerve implant and medication system shown in the drawings and described in detail herein, disclose steps in a process, arrangements of elements of particular construction, and configuration for illustrating preferred embodiments of structure and method of operation of the present invention. It is to be understood, however, that elements of different construction and configuration and different steps and process procedures and other arrangements thereof, other than those illustrated and described, may be employed for the implant device and method with the spirit of this invention.

As such, while the present invention has been described herein with reference to particular embodiments thereof, a latitude of modifications, various changes and substitutions are intended in the foregoing disclosure, and it will be appreciated that in some instance some features of the invention could be employed without a corresponding use of other features without departing from the scope of the invention as set forth in the following claims. All such changes, alternations and modifications as would occur to those skilled in the art are considered to be within the scope of this invention as broadly defined in the appended claims.

What is claimed is:

1. An apparatus for implant into an eye for treatment of a patient comprising:
    a body, said body having a sidewall;
    said sidewall defining an exterior surface, said exterior surface defining an exterior dimension for said body;
    said sidewall defining an internal cavity of said body;
    said internal cavity adapted to hold medicine therein;
    means for a controlled disbursement of said medicine from said internal cavity, to tissue surrounding said body portion, when said body is engaged within the eye of a patient;
    said exterior dimension of said body dimensioned for a frictional engagement in a cup-like depression of the optic nerve of said patient; and
    whereby said body when implanted in said cup like depression of said optic nerve of said patient, is maintained in a mounted position by said frictional engagement and said medicine is disbursed to said tissue of said eye.

2. A method of placing an ocular implant including an apparatus according to claim 1, for delivery of medicine to a patient, comprising the steps of:
    ascertaining the dimensions of a naturally existing cup like depression in the optic nerve of a patient;
    determining an optimum said exterior dimension for an implant in which said exterior surface of said implant will achieve a frictional engagement with said cup like depression when inserted therein in a mounted position;
    acquiring an implant having said optimum exterior dimension;
    ascertaining a medicine to be housed by said internal cavity of said implant for said disbursement to said tissue of said patient;
    ascertaining that said medicine is within said internal cavity; and
    placing said implant into said mounted position in said patient.

3. The apparatus for implant into an eye of claim 1 wherein said means for a controlled disbursement of said medicine from said internal cavity comprises an aperture in said sidewall.

4. The apparatus for implant into an eye of claim 1 wherein said means for a controlled disbursement of said medicine from said internal cavity comprises a semipermeable membrane in said sidewall.

5. The apparatus for implant into an eye of claim 1 additionally comprising:
    means to allow refilling of said internal cavity with said medication while said implant is mounted in said eye.

6. The apparatus for implant into an eye of claim 1 additionally comprising:
    said body formed of biodegradable material; and
    said biodegradable material absorbable by the patient subsequent to disbursement of said medicine therefrom whereby said body once implanted will dissolve over time and need not be removed surgically.

7. The apparatus for implant into an eye of claim 1 additionally comprising:
    said internal cavity being refillable with said medicine by a hypodermic needle communicating through said sidewall.

8. A method of placing an ocular implant including an apparatus according to claim 7, for delivery of medicine to a patient, comprising the steps of:
    ascertaining when a refill of said medicine in said internal cavity is needed; and
    employing said hypodermic needle to communicate additional said medicine to said internal cavity.

9. The apparatus for implant into an eye of claim 7 wherein said means for a controlled disbursement of said medicine from said internal cavity comprises an aperture in said sidewall.

10. The apparatus for implant into an eye of claim 7 wherein said means for a controlled disbursement of said medicine from said internal cavity comprises a semipermeable membrane in said sidewall.

* * * * *